United States Patent
Cassou et al.

[11] Patent Number: 5,582,602
[45] Date of Patent: Dec. 10, 1996

[54] FILTERING COLLECTING DEVICE FOR A VISCOUS FLUID SUCH AS A SEMINAL FLUID AND PORTABLE ELECTRIC APPARATUS COMPRISING SUCH A DEVICE

[75] Inventors: Robert Cassou, Aubigny Sur Nere; Maurice Cassou, Mortagne Au Perche; Bertrand Cassou, L'Aigle; Jean-Pierre Brillard, Joue Les Tours; Laurent Raulie, Saint-Herve, all of France

[73] Assignee: Societe d'Etudes, de Gestion, d'Engineering, L'Aigle, France

[21] Appl. No.: 233,827

[22] Filed: Apr. 26, 1994

[30] Foreign Application Priority Data

Apr. 26, 1993 [FR] France .................. 93 04904

[51] Int. Cl.⁶ .................................. A61M 1/00
[52] U.S. Cl. .................................. 604/319; 128/760
[58] Field of Search ...................... 604/317–321, 604/131, 140, 257; 119/14.47, 174; 128/760, 768; 137/205

[56] References Cited

U.S. PATENT DOCUMENTS

| 3,872,869 | 3/1975 | Randolph et al. |
| 4,083,706 | 4/1978 | Wiley |
| 4,402,687 | 9/1983 | Denty et al. |
| 4,957,492 | 9/1990 | McVay .................... 604/319 |

FOREIGN PATENT DOCUMENTS 0358302  3/1990  European Pat. Off.

*Primary Examiner*—John G. Weiss
*Assistant Examiner*—Dennis Ruhl
*Attorney, Agent, or Firm*—Young & Thompson

[57] ABSTRACT

A device for collecting seminal fluid, comprises a collecting container (1) on which is mounted an adaptor (2) provided with a cannula (3) for sucking up the seminal fluid under the effect of a partial vacuum. The device further includes an adaptor sleeve (5) interposed between the container (1) and the adaptor (2). The sleeve comprises a chamber (10) in communication with the adaptor (2) in which chamber a filter (11) for the seminal fluid is located. A pipe (16) for sucking up the fluid and having a first flared end portion (17) emerges on the filter (11) and a second end portion (18) emerges in the container via a projection (19) extending axially beyond the end (20) of the sleeve pointing towards the container. A sucking-up duct (21) intended to be connected to a source of partial vacuum terminates at the end (2) of the sleeve inside the container in order to generate, within the container (1), a partial vacuum intended to bring about the sucking-up of the seminal fluid through the filter (11).

11 Claims, 3 Drawing Sheets

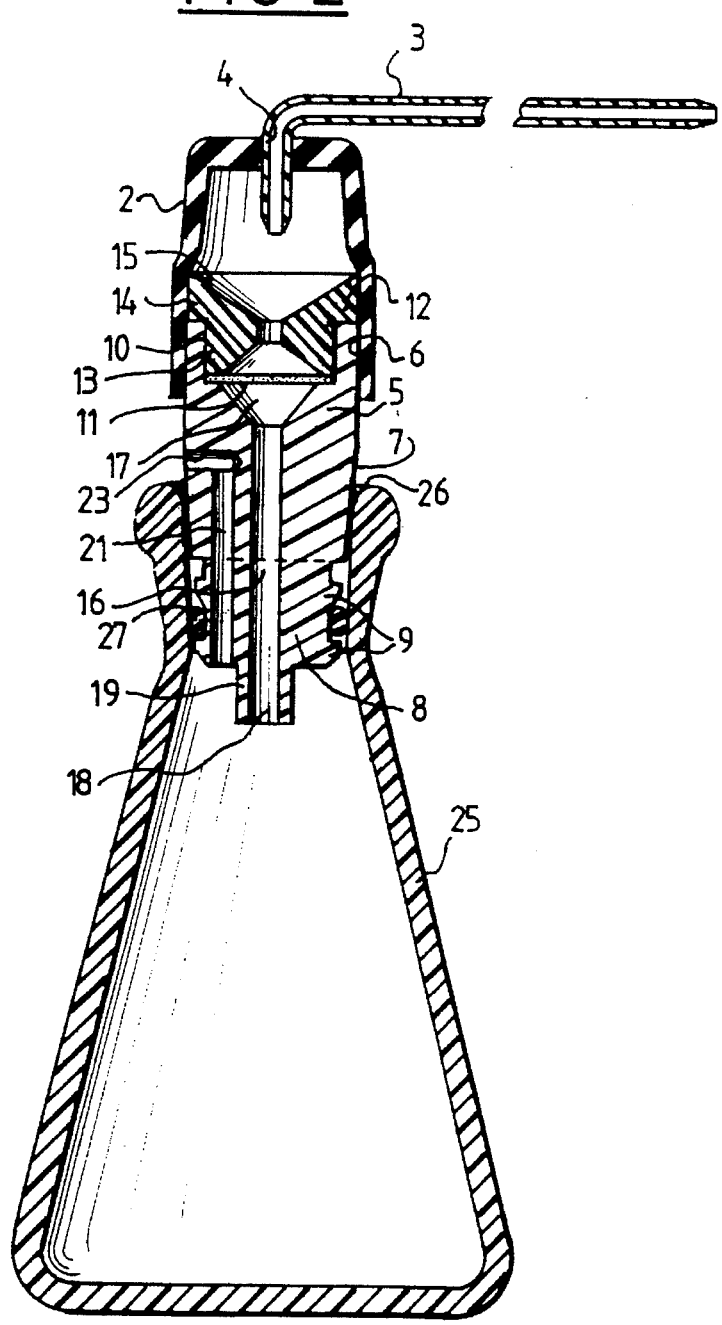
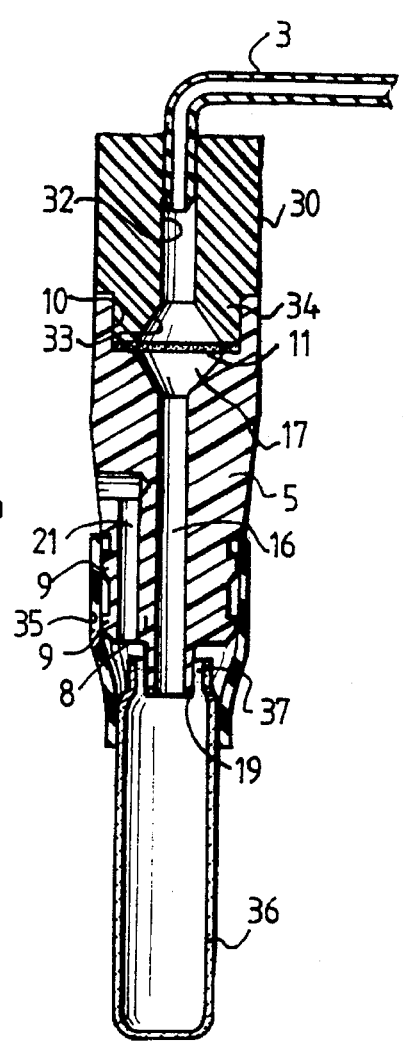
FIG. 2
FIG. 3

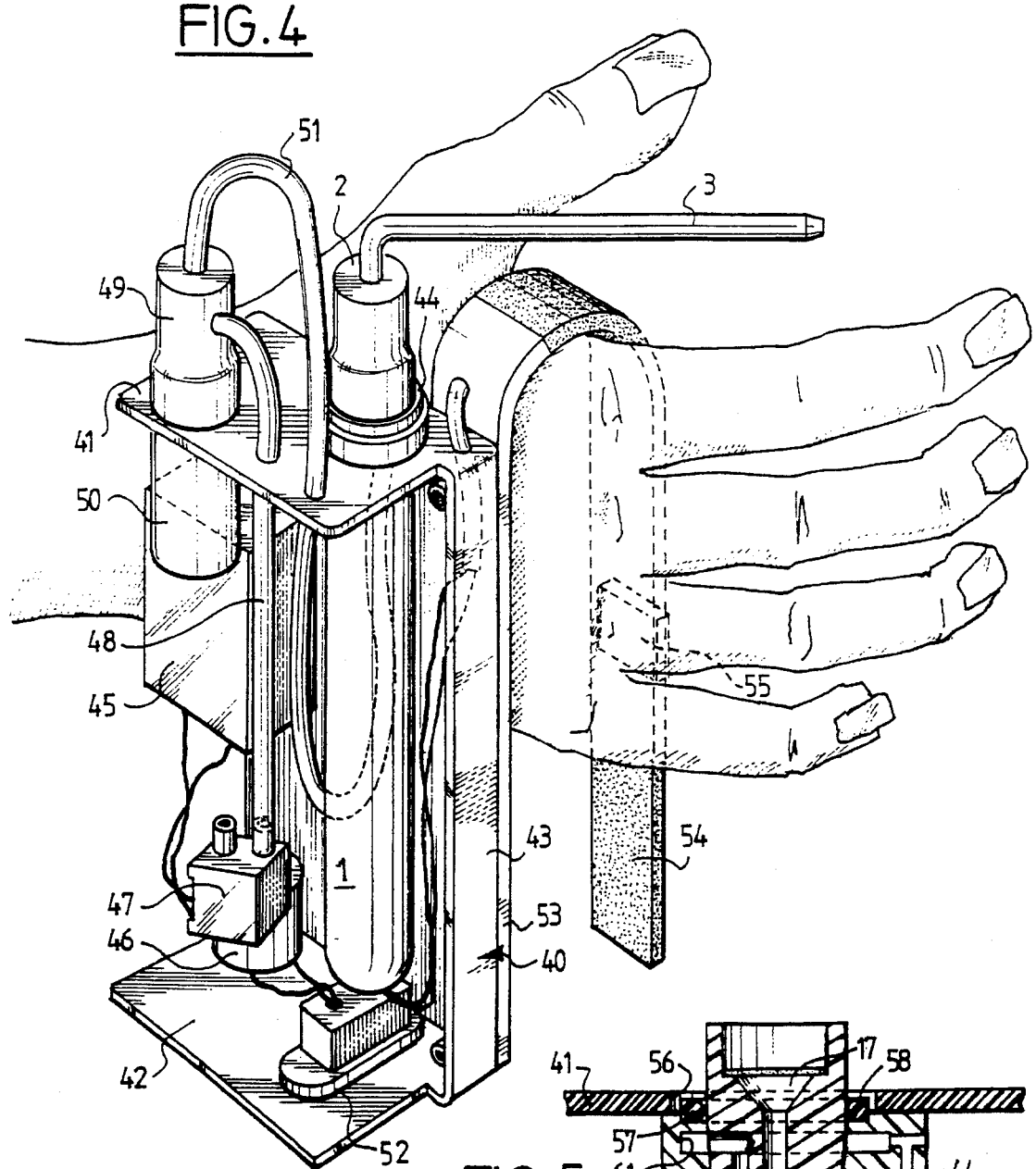
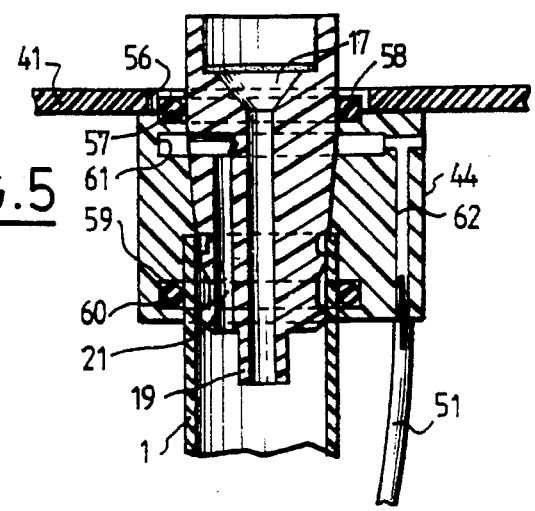

5,582,602

FILTERING COLLECTING DEVICE FOR A VISCOUS FLUID SUCH AS A SEMINAL FLUID AND PORTABLE ELECTRIC APPARATUS COMPRISING SUCH A DEVICE

FIELD OF THE INVENTION

The present invention relates to devices for collecting seminal fluid from animals and relates more particularly to a collecting device of the suction type using partial vacuum.

BACKGROUND OF THE INVENTION

The collection of seminal fluid, for example of birds, has, to date, been carried out with the aid of a collecting container equipped with a funnel above which an operator proceeds to manipulate the animal.

From French Patent no. 82 01 171 of Jan. 26, 1982, filed in the names of Messrs. Robert, Maurice and Bertrand CASSOU, a partial-vacuum collecting device is also known made up of a flexible cap covering a collecting container, the flexible cap being provided with a central orifice in which a cannula for sucking up the seminal fluid is mounted, and with a lateral orifice in which a tube for creating a partial vacuum in the container is engaged, this tube being connected to a pump or to an oral sucking adaptor.

These known devices exhibit the essential drawback of gathering, in the collecting container, a product containing foreign bodies such as dust, plumage debris, particles of food, grains of sand, droppings, which contaminate to a greater or lesser extent, particularly when the user massages too quickly or even violently.

Moreover, owing to the impurities contained especially in the seminal fluid, these known devices do not allow sterile products for preserving the semen to be added to the collecting container.

SUMMARY OF THE INVENTION

The invention aims to overcome the drawbacks of the known devices by creating a device for collecting seminal fluid which makes it possible to obtain, in the collecting container, a seminal fluid which is free of any impurity and consequently ready to be mixed with a preservative product or diluent.

Its subject is therefore a device for collecting a viscous fluid such as a seminal fluid, comprising a collecting container on which is mounted an adaptor provided with a cannula for sucking up the fluid under the effect of a partial vacuum, characterized in that it further includes an adaptor sleeve interposed between the container and the adaptor, the said sleeve comprising a filter in communication with the adaptor on the one hand and with the collecting container on the other hand, and a sucking-up duct intended to be connected to a source of partial vacuum in order to generate, within the container, a partial vacuum intended to bring about the sucking-up of the fluid through the said filter.

The subject of the invention is also an apparatus for collecting a viscous fluid such as a seminal fluid, characterized in that it includes a fluid-collecting device provided with a sucking-up duct intended to be connected to a source of partial vacuum, the collecting device being engaged removably in a casing by means of a fitting ring fixed into a wall of the casing and including means for leaktight connection of the sucking-up duct of the collecting device with a source of partial vacuum comprising a pump and an electric motor for actuating this pump, which are also contained in the casing, the electric motor being connected to a power supply battery, whereas the pump is connected by a pipe to the fitting ring.

BRIEF DESCRIPTION OF THE DRAWINGS

The invention will be better understood with the aid of the description which will follow, given solely by way of example and made with reference to the appended drawings, in which:

FIG. 2 is an elevation and sectional view of a second embodiment of the filtering collecting device for a seminal fluid according to the invention;

FIG. 3 is an elevation and sectional view of a third embodiment of the device for collecting seminal fluid according to the invention;

FIG. 4 is a diagrammatic perspective view of a device for collecting seminal fluid of the electric and portable type; and FIG. 5 is a partial sectional view of the ring for fitting the collector of FIG. 4.

DETAILED DESCRIPTION OF THE INVENTION

Figure 1:
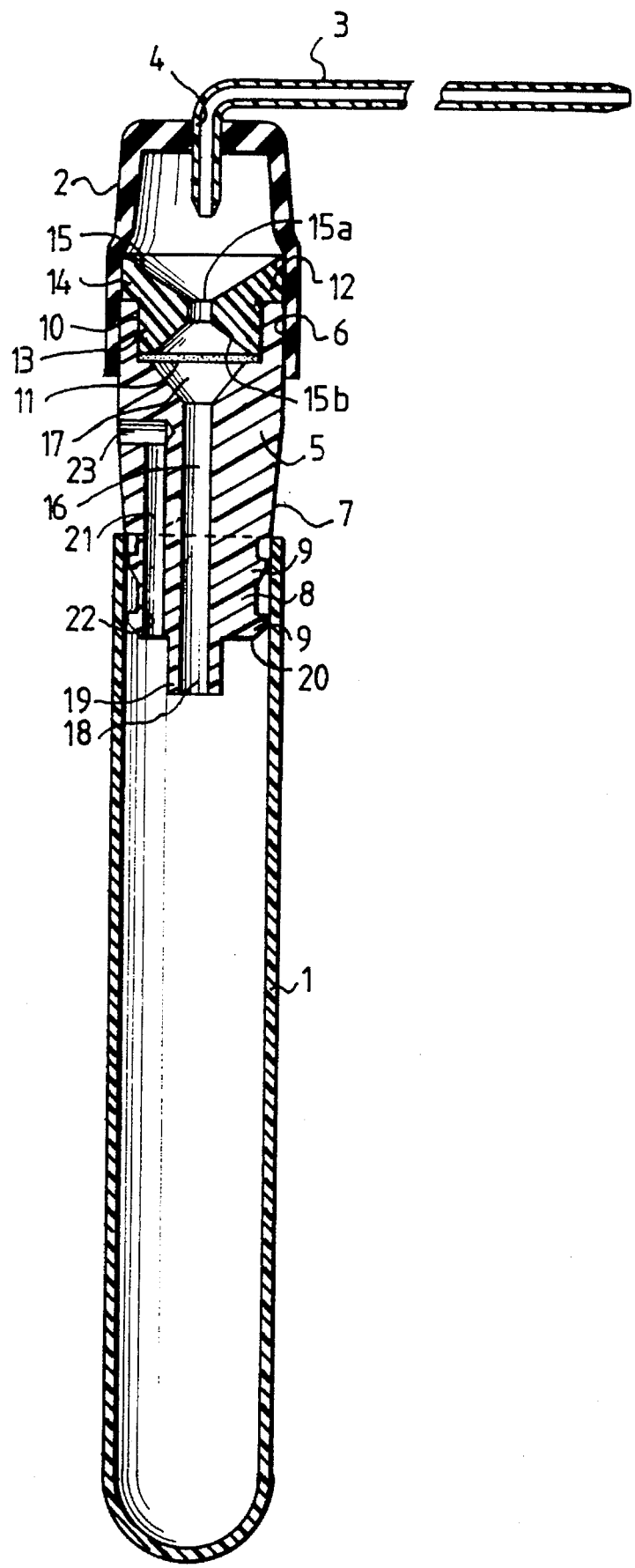
FIG. 1 is an elevation and sectional view of a first embodiment of the device for collecting seminal fluid according to the invention.

The filtering collecting device for a seminal fluid, represented in FIG. 1, mainly includes a collecting container 1 made up of a test tube on which is mounted an adaptor 2 made up of a flexible cap made of plastic provided with a sucking-up cannula or collection tube 3, engaged in an axial hole 4 in the flexible cap.

Between the cap 2 and the tube 1 is interposed an adaptor sleeve 5 which includes a cylindrical outer lateral surface 6 for receiving the open end of the flexible cap 2, this surface being extended by a slightly frustoconical outer lateral surface 7, the function of which will be explained later.

At its opposite end from the flexible cap 2, this end being intended to be engaged in the test tube 1, the adaptor sleeve 5 includes a portion 8 provided with peripheral ribs 9 for gripping into the test tube, these ribs being inclined in the direction of insertion of the sleeve into the tube and intended, thereby, to prevent the sleeve from being removed after it has been engaged.

At its end near the flexible cap 2, the adaptor sleeve includes a chamber 10 open towards the flexible cap 2 and in which is mounted a filter 11 for the seminal fluid.

The filter 11 is of the type with a very fine mesh size of dimension less than 100 µ for filtering substances or fluids which are less fluid than water. The dimension of the meshes of the filter is matched to the product to be filtered.

The filter is advantageously a filter made of polyester or polyamide with a single thread, therefore without fluffiness or fibres which would risk being mixed with the seminal fluid.

The material of the filter is not wettable and is non-toxic.

In the example represented in FIG. 1, the filter 11 is held in the chamber 10 by a fixing connector 12 which includes a skirt 13 in contact with the lateral surface of the chamber 10 and applying the edge of the filter against the bottom of the said chamber and a rim 14, the diameter of which is equal to the outside diameter of the lateral surface 6 of the sleeve 5. The rim 14 internally defines a flared receptacle 15 for the semen, extending immediately below the end of the sucking-up cannula 3 engaged in the flexible cap 2 and terminating at a cylindrical restriction 15a which in turn communicates with a frustoconical chamber 15b which widens out the restriction 15a for the purpose of distributing the fluid over the entire useful surface of the filter 11. The restriction 15a prevents the air from passing at the same time as the fluid, despite modifications in inclination of the collecting device while it is being used.

In the adaptor sleeve 5 an axial pipe 16 is formed for sucking up the seminal fluid, which includes a flared end portion 17 communicating with the chamber 15b through the filter 11, and an end portion 18 emerging in the test tube 1 via a projection or snout 19 extending beyond the end 20 of the sleeve 5 inside the test tube.

In the sleeve 5 a bent duct 21 is further formed for placing the inside of the test tube in communication with a source of partial vacuum which has not been represented. The duct 21 includes an axial portion 22 parallel to the sucking-up pipe 16 which emerges in the end 20 of the adaptor sleeve 5 inside the test tube, that is to say set back from the end portion 18 of the pipe 16 for sucking up the seminal fluid, and a radial portion 23 which emerges in the lateral surface of the adaptor sleeve 5, so as to be placed in communication with the source of partial vacuum which has not been represented.

By virtue of this arrangement, when a partial vacuum is created inside the test tube 1 by suction through the duct 21, this partial vacuum leads to a suction from the bottom of the adaptor sleeve 5 through the filter 11, the inside of the flexible cap 2 and the sucking-up cannula 3.

The fact that the ends 18 of the pipe 16 for sucking up the seminal fluid projects with respect to the end of the sucking-up duct 21 connected to the source of partial vacuum prevents part of the fluid sucked up by the pipe 16 from penetrating into the sucking-up duct 21 connected to the source of partial vacuum.

The flexible cap 2 which is produced from a transparent material allows a visual check on the gathering of the seminal fluid.

By virtue of the presence of the filter 11, the liquid gathered has had removed from it any foreign bodies, such as dust, plumage debris, particles of food, grains of sand, which contaminate to greater or lesser degrees, and particularly droppings in the case of the gathering of bird semen.

The connector 12 for fixing the filter 11 directs the semen onto the filter and the widened end portion 17 of the sucking-up duct 16, of which the end in contact with the filter 11 exhibits a cross-section practically equal to the useful surface of this filter, makes it possible to filter the semen over a wider filter surface, which thereby increases the number of doses filtered.

The filter 11 may be changed rapidly between two gatherings without a great amount of manipulation. According to one variant, it may also be rendered integral with the filter chamber 10, for example by bonding or welding, so as to prevent soiling it with the fingers in the case where a completely disposable adaptor or filter sleeve is used.

As indicated previously, the device for collecting seminal fluid described with reference to FIG. 1, equipped with its adaptor and filter sleeve, may be connected to an oral or electric suction system.

The filter chamber 15b delimited by the skirt 13 of the ring 12 exhibits a relative small volume thus allowing the animal semen to cover the filtering zone of the filter 11 more quickly. Since the air is not able to pass through the filter owing to the presence of the restriction 15a, the filtration then starts of the semen which will be directed towards the test tube 1 in which the vacuum has been created by suction in the way described previously.

The device for collecting seminal fluid represented in FIG. 2 is, in every aspect, similar to that described with reference to FIG. 1, except for the fact that the collecting container of the latter is made up of a conical flask 25.

In order to allow the adaptor sleeve 5 to be mounted in leaktight fashion in the neck 26 of the container 25, the sleeve is engaged in the neck 26 so that its frustoconical lateral surface 7 is in contact with the complementary frustoconical surface of the neck 26. An O-ring 27 is fixed on the end of the sleeve 8 including the ribs 9 and engaged in a groove formed between two of these ribs.

The device for collecting seminal fluid represented in FIG. 3 differs from those described with reference to FIGS. 1 and 2 in that, instead of the flexible cap 2 bearing the sucking-up cannula 3 of the foregoing embodiments, it includes a rigid cap 30 alone fulfilling the functions of the flexible cap 2 and of the connector 12 for fixing the filter of the embodiment of FIG. 1.

It is made up of a solid component, at the centre of which emerges a duct 32 in which the sucking-up cannula 3 is engaged.

At its opposite end, the axial duct 32 emerges in a frustoconical chamber 33 situated just above the filter 11 placed in the axial chamber 10 of the adaptor sleeve 5. The chamber 33 widens the duct 32 in order to distribute the fluid over the entire useful surface of the filter. The duct 32 constitutes a restriction preventing the air from passing at the same time as the semen despite modifications in the inclination of the collecting device while it is being used.

The rigid cap 30 includes, around the frustoconical chamber 33, a skirt 34 which is used to immobilize the filter 11.

The adaptor sleeve 5 is of identical construction to that of the sleeves of the embodiments of FIGS. 1 and 2.

Its end 8 provided with annular ribs 9 receives a flexible sleeve 35 for connection with a tubular container of small cross-section, such as an ampoule 36 with a ready broken-off end which in this case fulfils the function of collecting container. The projection 19 on the fitting sleeve 5 is engaged in the neck of the ampoule 36 with a ready broken-off end with a clearance 37 which makes it possible to create, within the container, the partial vacuum necessary for sucking up by means of the axial sucking up duct 21 connected to a source of partial vacuum which is not represented, similar to the one described within the context of the description of the foregoing embodiments.

It can be seen that, in the embodiment of FIG. 3, the projection or snout 19 interacting with the relatively narrow neck of the ampoule 36 with a ready broken-off end prevents the semen from rising back up through the sucking-up duct 21.

The flexible sleeve 35 fits in leaktight fashion on the one hand over the end 8 of the fitting sleeve 5 and, on the other hand, over the perimeter of the ampoule 36 with a ready broken-off end slightly below its neck.

In the present embodiment, the semen is filtered more quickly owing to the presence of the narrow duct 32 in the rigid plug 30 which eliminates the passage of air between the semen and the edges of this pipe, even when a thick and viscous substance which sticks to the walls has to be sucked up and filtered.

The filling of the filter chamber also takes place more quickly, so that the flow rate of the filtering system is increased.

Moreover, the rigid cap 30, the axial duct 32 of which is directly connected to the sucking-up pipe 16 of the fitting sleeve 5, does not interrupt the arrival of the semen in the filtering chamber, regardless of the angle of the cannula 3 for sucking up semen of the collecting device.

It can therefore be seen that, by virtue of the arrangement which has just been described, the fitting or filtering sleeve 5 is designed to fit over various types of semen-collecting containers.

Thus, this sleeve 5 constitutes a multi-function component of the device according to the invention.

Reference will now be made to FIG. 4 in which a portable and self-contained electric apparatus for collecting seminal fluid according to the invention has been represented.

This apparatus, the protective cover of which has been removed for greater clarity, includes a body 40 made from an insulating material which includes two end walls 41, 42 extending perpendicularly to a base 43. In one of the end walls 41 of the body 40 is mounted a removable ring 44 for fitting a collecting device with filtration for fluid such as that described with reference to FIG. 1 or FIG. 3.

In the body 40 are further mounted a rechargeable battery 45, for example a 6- to 9-volt battery, connected to an electric motor 46 for actuating a vacuum pump 47 coupled by a pipe 48 to a flexible cap 49 which covers a decanting container 50 and which is in turn coupled by a flexible pipe 51 to the fitting ring 44 in a way which will be described with reference to FIG. 5.

On the end wall 42 opposite the one carrying the fitting ring 44, the casing 40 bears an electric socket 52 for connection to a battery charger which is not represented.

On the face of the base 43 of the body 40 opposite the end sides 41, 42 is mounted a grip 53 in the form of a U or crook which, on its free branch 54, bears a switch 55 for controlling the motor 46 for driving the vacuum pump 47, it being possible for the said switch to be actuated by the fingers of the hand of the user while the back of this hand is in contact with the bottom 43 of the casing 40 in the way represented in FIG. 5.

The presence of the crook-shaped grip 53 makes it possible to free the five fingers of the hand in order to proceed with the massaging of the animals whilst having available a sucking-up system for gathering the bird seminal fluid.

Such a device is particularly lightweight and self-contained and has no electric flex, or cumbersome pipework.

The decanting vessel 50 which adjoins the collecting tube 1 prevents any impurity or foreign fluid from being able to hinder the correct operation of the pump 47.

The fitting ring 44 will now be described with reference to FIG. 5.

It is mounted in the end wall 41 of the casing 40 via an axial rim 56 in which is formed a first annular groove 57 receiving a first O-ring 58. At its opposite end from the O-ring 58, the ring 44 includes a second annular groove 59 in which is mounted a second O-ring seal 60.

Between the two O-rings 58 and 60, an annular chamber 61 is formed in which there emerges a sucking-up pipe 62 connected to the flexible pipe 51 for connection with the suction pump via the decanter 50.

When the collecting device represented in FIG. 1 is mounted removably in the fitting ring 44 of the apparatus of FIG. 4, the outer lateral wall of the fitting sleeve 5 is located in the ring 44 so that the O-rings 58 and 60 of this ring constitute, together with this lateral wall, a leaktight space connecting the orifice 23 of the sucking-up duct of the fitting sleeve 5 with the annular chamber 61 and the sucking-up duct 62 of the ring 44, which, when the pump is started up, allows the creation, in the collecting container 1, of the partial vacuum necessary for sucking up the seminal fluid via the sucking-up cannula 3, the filter 11 and the sucking-up pipe 16 formed in the fitting sleeve 5.

When one operation of collecting in a collecting device has ended, this device is removed from the apparatus and replaced by another without the need for disconnections by hand which would risk giving rise to soiling, a source of contamination.

Of course, the test tube may contain a product for diluting or preserving the seminal fluid, allowing automatic dilution.

The components of the collecting device according to the invention have been designed so as to be entirely mouldable and may consequently be considered as disposable products, avoiding the need for daily cleaning and sterilization.

It can be seen that, by virtue of the arrangement described with reference to FIGS. 4 and 5, an oral sucking-up system which gives rise to the risks of contamination by the introduction of saliva into the medium to be collected is replaced by lightweight, handleable and non-contaminating suction means and that, by virtue of the use of an apparatus with rechargeable battery, the use of a high-voltage pump connected to the mains is eliminated.

In the embodiments which have just been described, the invention is considered as being applied to the collection of seminal fluid.

It is possible, however, to envisage using the collecting apparatus and device of the invention for collecting other viscous fluids.

I claim:

1. Device for collecting a viscous fluid such as seminal fluid comprising a collecting container (1; 25; 36) on which is mounted an adaptor (2; 30) provided with a cannula (3) for sucking up the fluid under the effect of a partial vacuum, an adaptor sleeve (5) interposed between the container (1; 25; 36) and the adaptor (2; 30), the said sleeve comprising a filter (11) in communication with the adaptor (2; 30) on the one hand and with the collecting container (1; 25; 36) on the other hand, and in said sleeve a vacuum duct (21) intended to be connected to a source of partial vacuum in order to generate, within the container, a partial vacuum intended to bring about the sucking-up of the fluid through the said filter (11), said adaptor sleeve (5) comprising a chamber (10) in communication with the adaptor (2; 30) in which chamber the filter (11) for the fluid is located, a pipe (16) for sucking up the fluid comprising a first flared end portion (17) emerging on the filter (11) and a second end portion (18) emerging in the container via a projection (19) extending axially beyond an end (20) of the sleeve inside the container and said vacuum duct (21) terminating at the end (20) of the sleeve inside the container.

2. Collecting device according to claim 1, characterized in that the collecting container is a test tube (1) and the adaptor sleeve (5) includes a portion (8) engaged in the test tube and provided with annular gripping ribs (9) having inclined engagement surfaces.

3. Collecting device according to claim 1, characterized in that the collecting container is a conical flask (25) having a neck (26) and the adaptor sleeve (5) includes a frustoconical portion (7) engaged in the neck (26) of the conical flask and a portion (8) provided with annular ribs (9), at least one O-ring seal (27) being mounted on the said portion (8) of the adaptor sleeve in a groove defined between two of the ribs (9).

4. Collecting device according to claim 1, characterized in that the collecting container is a tubular container of small cross-section (36) and in that it includes a flexible sleeve (35) for connection of the said tubular container (36) to said adaptor sleeve, this flexible sleeve fitting in leaktight fashion on the one hand over a portion (8) of the adaptor sleeve (5) pointing towards the said container (36) and, on the other hand, over said container (36), a projection (19) via which the sucking-up pipe (16) of the adaptor sleeve (5) emerges into the container being engaged with a clearance (37) in the neck of the said container (36).

5. Collecting device according to claim 4, characterized in that the said collecting container of small cross-section (36) is an ampoule with a readily breakable end.

6. Collecting device according to claim 1, characterized in that the adaptor (2) provided with the cannula for sucking up the liquid is a cap made of a flexible material mounted on a lateral outer wall (6) of the adaptor sleeve.

7. Collecting device according to claim 6, characterized in that it further includes a connector (12) for fixing the filter (11) which includes a skirt (13) in contact with a lateral surface of the chamber (10) of the adaptor sleeve (5) and applying the edge of the filter against the bottom of the said chamber and a rim (14) internally defining a flared receptacle (15) for the seminal fluid and extending immediately below the end of the sucking-up cannula (3) engaged in the flexible cap (2), the receptacle terminating at a restriction (15a) which in turn communicates with a chamber (15b) ensuring the distribution of the fluid over the entire useful surface of the filter.

8. Collecting device according to claim 1, characterized in that the adaptor (30) provided with the cannula for sucking up the seminal fluid is a rigid cap including a skirt (34) engaged in the chamber (10) of the adaptor sleeve and holding the filter (11), the said rigid cap comprising a narrow and axial duct (32) in which is engaged the sucking-up cannula (3), the said axial duct emerging in a frustoconical chamber (33) situated just above the filter (11) and ensuring the distribution of the fluid over the entire useful surface of the filter.

9. Collecting device according to claim 1, characterized in that the filter (11) is fixed into the chamber (10) of the adaptor sleeve (5) by adhesive bonding or welding.

10. Collecting device according to claim 1, characterized in that the filter (11) is a filter with a very fine mesh, made of a single thread, which cannot be wetted and the dimension of which is adapted to the fluid to be filtered.

11. Collecting device according to claim 10, characterized in that the filter (11) is made from a non-toxic polyester or polyamide, with a mesh size less than 100μ.

* * * * *

UNITED STATES PATENT AND TRADEMARK OFFICE
CERTIFICATE OF CORRECTION

PATENT NO. : 5,582,602
DATED : December 10, 1996
INVENTOR(S) : Robert CASSOU et al.

It is certified that error appears in the above-indentified patent and that said Letters Patent is hereby corrected as shown below:

On the title page:

In Item [75] Inventors: change the surname of the fifth inventor, from "Raulie" to --Raulic--.

Signed and Sealed this

Twenty-fifth Day of February, 1997

Attest:

BRUCE LEHMAN

Attesting Officer

Commissioner of Patents and Trademarks